United States Patent
Kullik et al.

(10) Patent No.: US 6,745,765 B2
(45) Date of Patent: Jun. 8, 2004

(54) ANESTHETIC CONTAINER WITH METERING ELEMENTS

(75) Inventors: Götz Kullik, Lübeck (DE); Jochim Koch, Ratzeburg (DE)

(73) Assignee: Dräger Medical AG & Co. KGAA, Lübeck (DE)

( * ) Notice: Subject to any disclaimer, the term of this patent is extended or adjusted under 35 U.S.C. 154(b) by 165 days.

(21) Appl. No.: 10/071,998

(22) Filed: Feb. 7, 2002

(65) Prior Publication Data

US 2003/0005930 A1 Jan. 9, 2003

(30) Foreign Application Priority Data

May 22, 2001 (DE) .......................... 101 24 886

(51) Int. Cl.[7] .................... A61M 15/00; A61M 16/00
(52) U.S. Cl. ................................. 128/203.14
(58) Field of Search ................ 128/203.12, 203.13, 128/203.25, 203.14, 205.14, 205.18, 204.19, 204.21, 205.13, 203.19; 222/95, 327, 387, 389, 391, 41

(56) References Cited

U.S. PATENT DOCUMENTS

| | | | | |
|---|---|---|---|---|
| 4,714,462 A | * | 12/1987 | DiDomenico | 604/67 |
| 4,779,770 A | * | 10/1988 | Herold | 222/391 |
| 5,242,403 A | * | 9/1993 | Falb et al. | 604/113 |
| 5,243,973 A | * | 9/1993 | Falb et al. | 128/203.27 |
| 5,293,865 A | * | 3/1994 | Altner et al. | 128/203.12 |
| 5,571,071 A | * | 11/1996 | Shapiro | 600/187 |
| 5,628,305 A | * | 5/1997 | Melker | 128/202.29 |
| 5,647,346 A | * | 7/1997 | Holscher | 128/202.22 |
| 6,002,337 A | * | 12/1999 | Palfey et al. | 340/606 |
| 6,286,505 B1 | * | 9/2001 | Psaros | 128/203.12 |
| 2002/0069876 A1 | * | 6/2002 | Loser et al. | 128/203.19 |

FOREIGN PATENT DOCUMENTS

DE  37 20 326 C2  12/1988

* cited by examiner

Primary Examiner—Henry Bennett
Assistant Examiner—Sabrina Dagostino
(74) Attorney, Agent, or Firm—McGlew and Tuttle, P.C

(57) ABSTRACT

A reusable anesthetic container (1) has an anesthetic reserve space (2), which is provided with at least one movable wall element (3). The wall element (3) can be caused to follow the liquid anesthetic volume. In one embodiment, the movable wall element (3) is designed as a piston, which is caused to follow the anesthetic volume via a toothed piston rod (9). An elastomer ring is preferably provided on the storage container as a detent pawl for the piston rod (9). The anesthetic container (1) has a first metering element (5), which is actuated inductively by means of a complementary second metering element (6) cooperating with another metering element on the anesthesia apparatus (7) for metering the anesthetic.

26 Claims, 2 Drawing Sheets

ANESTHETIC CONTAINER WITH METERING ELEMENTS

FIELD OF THE INVENTION

The present invention pertains to an anesthetic container with an anesthetic reserve space.

BACKGROUND OF THE INVENTION

Anesthetic containers in the form of glass bottles with universal screw cap and a coding collar for special filling devices are filled with an anesthetic, in general, at the anesthetic producer. These prior-art anesthetic containers in the form of glass bottles are transported to the hospital, e.g., in a Styropor package for protection against breakage. The anesthetics are filled there hitherto into the correct anesthetic metering unit and calibrated for one anesthetic only either by means of a special, coded filling tube or filling adapter or by pouring into an open filling funnel.

A filling adapter for filling an anesthetic metering unit with anesthetic is shown in DE 37 20 326 C2.

Both the filling of an anesthetic metering unit by means of a filling tube or filling adapter or by means of a filling funnel is cumbersome, time-consuming. This is especially so in the case of the use of a filling funnel and is linked with the risk for overdosage of the anesthetic due to the possible confusion of the anesthetic added. In addition, the undesired evaporation of the anesthetic into the air of the room is hazardous to ones health.

The anesthetic containers used hitherto are usually not refilled and are disposed of with the domestic waste of the hospital or in the waste glass container.

SUMMARY AND OBJECTS OF THE INVENTION

The object of the present invention is consequently to provide a reusable anesthetic container, which can be filled with anesthetic at the anesthetic producer and subsequently stored and transported in order to be plugged into an anesthesia apparatus and to dispense anesthetic to the anesthesia apparatus in a metered manner and finally to be returned to the anesthetic producer for refilling with anesthetic in a closed cycle after it has released its anesthetic reserve.

According to the invention, an anesthetic container is provided with an anesthetic reserve space. The anesthetic reserve space has at least one movable wall element. The wall element can follow the liquid anesthetic volume.

One essential advantage of the anesthetic container according to the present invention with metering elements arises from the fact that there is no gas volume in the anesthetic storage space, so that a change in the ambient conditions, i.e., the temperature, the pressure or the filling level, has no effect on the anesthetic to be metered.

Another advantage of the anesthetic container according to the present invention is the physical separation between first functional elements, which are arranged on the anesthetic container itself, and complementary, second functional elements in the plug-in unit or plug-in place of the anesthesia apparatus, which first and second functional elements cooperate in order to ensure especially the correct coding and the accurate metering of the anesthetic.

The means for applying a force to the wall element to maintain the liquid anesthetic under pressure, as the wall element is caused to follow the surface of the volume of the liquid anesthetic, may include a mechanical device as well as an adjustable pressurized gas supply. A piston actuator as the mechanical element can also be provided for performing a displacement measurement of the piston corresponding to the position of the piston as well as a force measurement. The displacement measurement provides a filling sensor for sensing the filling level of the anesthetic reserve space.

Two exemplary embodiments of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
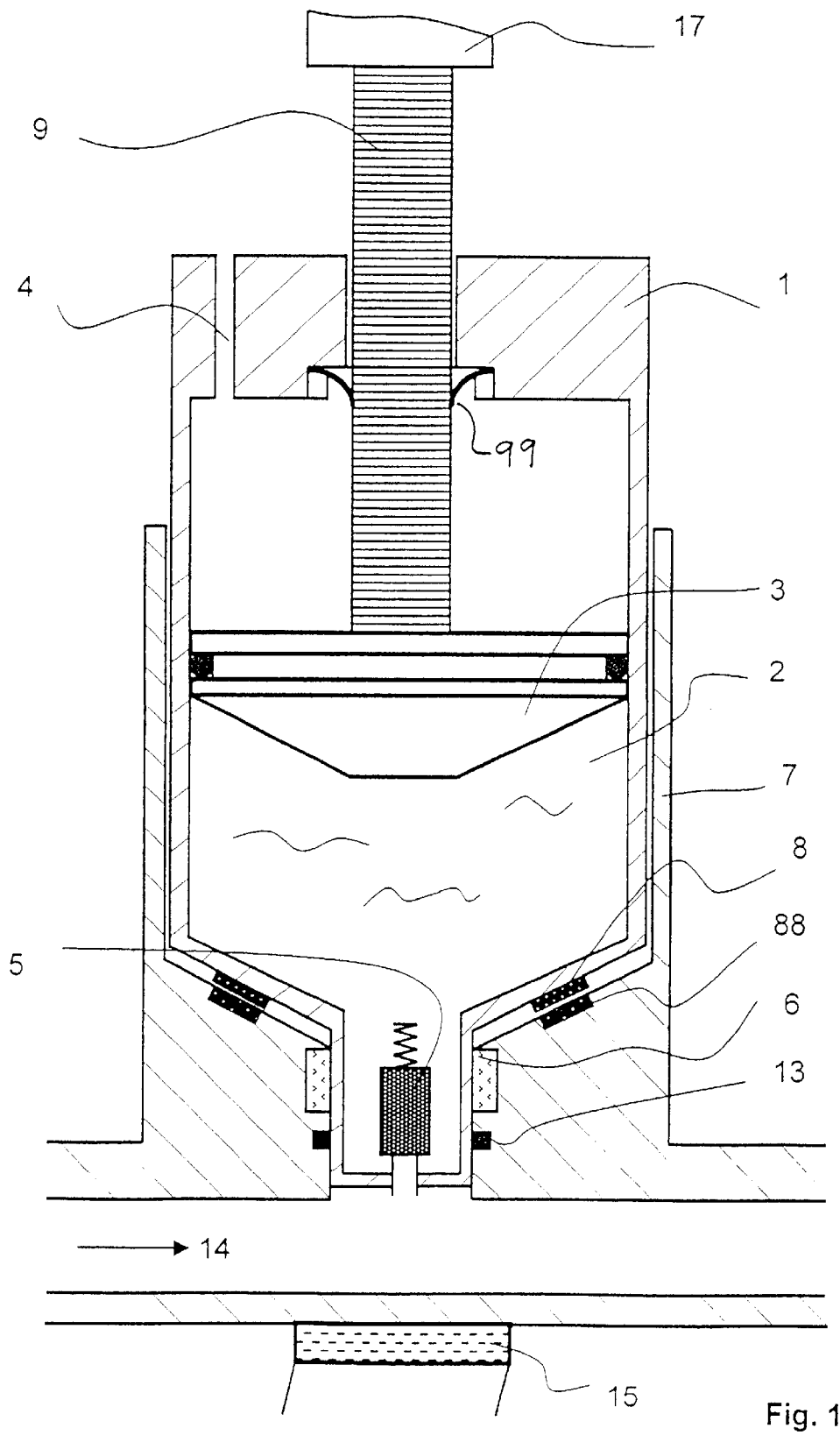
FIG. 1 is a sectional view of a first exemplary embodiment of an anesthetic container according to the present invention in a plug-in unit of an anesthesia apparatus.

Referring to the drawings in particular, the anesthetic container 1 in FIG. 1 is made of a material that is inert with respect to anesthetics, especially a metal. The anesthetic storage space 2 is filled with the particular liquid anesthetic and is provided with at least one movable wall element 3, especially in the form of a piston, which said wall element is able to follow the liquid anesthetic volume, so that no gas is present in the anesthetic storage space 2 during changes in the liquid volume. The changes in the volume of the liquid anesthetic during changes in the temperature and the atmospheric pressure are very small, i.e., negligible. In the exemplary embodiment according to FIG. 1, the anesthetic container 1 is provided with at least one ventilation opening 4 or a gas-permeable membrane, so that the pressure difference generated by the movable, volume-following wall element 3 in the anesthetic container 1 is compensated by the ambient atmosphere. The anesthetic may be metered both in a pressureless manner, e.g., with a micropump, or by admitting pressure to the liquid anesthetic and with a metering valve. If the anesthetic is metered in a pressureless manner, the movable wall element 3, of which there is at least one, must follow the change in the filling level of the anesthetic such that atmospheric pressure will always be present in the liquid anesthetic.

The handling of anesthetics, which already boil at room temperature, e.g., desflurane, is possible without a gas volume only if the liquid anesthetic is metered under pressure. It is necessary for this to fix the volume of the liquid anesthetic for the transportation or storage and to release it under load with an external pressure corresponding to a mechanical force by the movable wall element 3, of which there is at least one, in order to follow the changing filling level of the liquid anesthetic volume. The return movement of the wall element 3, of which there is at least one and which is designed especially as a piston, must be possible only during the filling operation, so that a corresponding mechanical safety device can be released. This safety device is blocked during the metering of the anesthetic and ensures that the fine-toothed piston rod 9 is moved only in the direction of the anesthetic, where an elastomer ring 99 is provided as the detent pawl.

Since the filling with anesthetic does not take place at the user any longer, but at the anesthetic producer, a special device can be used for this purpose and, in addition, the filling operation can take place under special conditions, which are below the boiling conditions in terms of temperature and pressure, i.e., at a low temperature and/or under increased pressure. Each anesthetic container 1 can be plugged into a plug-in place on the anesthesia apparatus 7. The plug-in place is not specific of the anesthetic and may be located in the fresh gas branch or in the breathing system. In case of metering into the breathing circuit 14 according to FIG. 1, the necessary heat of evaporation is supplied by a surface heated by means of a heater 15 in the breathing circuit or, as an alternative, by a tube heater.

The plug-in place has an electrical or preferably magnetic connection for the operation of the complementary, cooperating metering elements 5, 6; these are especially a valve body with an associated valve coil or an inductively actuated pump with a coil. By coding the anesthetic container 1 by means of microchip elements or by means of a transponder 8, 88, the correct assignment of the anesthetic container 1 with the selected anesthetic can be reliably ensured. Contrary to an anesthesia apparatus that operates with an anesthetic evaporator, the arrangement being described requires no fresh gas and is therefore ideally suitable for metering anesthetic into a completely closed breathing circuit of the anesthesia apparatus.

The user can store different anesthetics in a sealed manner in anesthetic containers 1 according to the present invention, which are adapted into the plug-in place on the anesthesia apparatus 7 when needed, so that the user never comes into contact with liquid anesthetic. When removing the anesthetic containers 1 according to the present invention, the metering unit, comprising the metering elements 5, 6, closes, so that even partially used, removed containers remain closed until the next use. In case of metering under pressure, as is shown in the figures, pressure information is necessary. Since this pressure of the anesthetic container 1 is imposed on the at least one movable wall element 3 of the anesthetic container 1, this pressure information can advantageously be obtained without contact with the anesthetic either by measuring the working pressure or by measuring the force on the movable wall element 3 represented as a piston.

The user can store different anesthetics in a sealed manner in anesthetic containers 1 according to the present invention, which are adapted into the plug-in place on the anesthesia apparatus 7 when needed, so that he never comes into contact with liquid anesthetic. When removing the anesthetic containers 1 according to the present invention, the metering unit, comprising the metering elements 5, 6, closes, so that even partially used, removed containers remain closed until the next use. In case of metering under pressure, as is shown in the figures, pressure information is necessary. Since this pressure of the anesthetic container 1 is imposed on the at least one movable wall element 3 of the anesthetic container 1, this pressure information can advantageously be obtained without contact with the anesthetic either by measuring the working pressure or by measuring the force on the movable wall element 3 represented as a piston.

Depending on the adjusted piston position corresponding to the anesthetic filling level, an alarm can be triggered for the user shortly before complete emptying, so that the anesthetic container 1 can be replaced with a filled replacement container in time. To measure the anesthetic temperature, a temperature sensor 13 is positioned either directly in the anesthetic container 1 or, as is shown in FIG. 1, at the plug-in place of the anesthesia apparatus 7 in good thermal contact with the anesthetic.

The piston rod 9 is fine-toothed and is secured in the particular position by means of an the elastomer ring 99 acting as a detent pawl, so that a pressure-controlled guiding of the piston directly based on the anesthetic volume is possible. The complementary, cooperating metering elements 5, 6 according to FIG. 1 form a valve that can be actuated electromagnetically. The valve body is arranged in the anesthetic container 1 and the valve coil is part of the plug-in place of the anesthesia apparatus 7. The filling with anesthetic at the anesthetic producer can also take place by actuation and via the metering elements 5, 6. The filling level measurement is performed as a displacement measurement in the piston actuating means 17 of the anesthesia apparatus 7 corresponding to the position of the piston, and the force measurement likewise takes place by means of the piston actuating means 17 of the anesthetic container 1. This piston actuating means 17 provides a displacement and/or force transducer detachably connected to the wall element 3. This piston actuating means 17 also provides a filling sensor for the filling level measurement.

There are no electric contacts between the anesthetic container 1 and the anesthesia apparatus 7 in the exemplary embodiment at all. The information for coding and the energy for actuating the valve are sent exclusively magnetically in an inductive manner.

Figure 2:
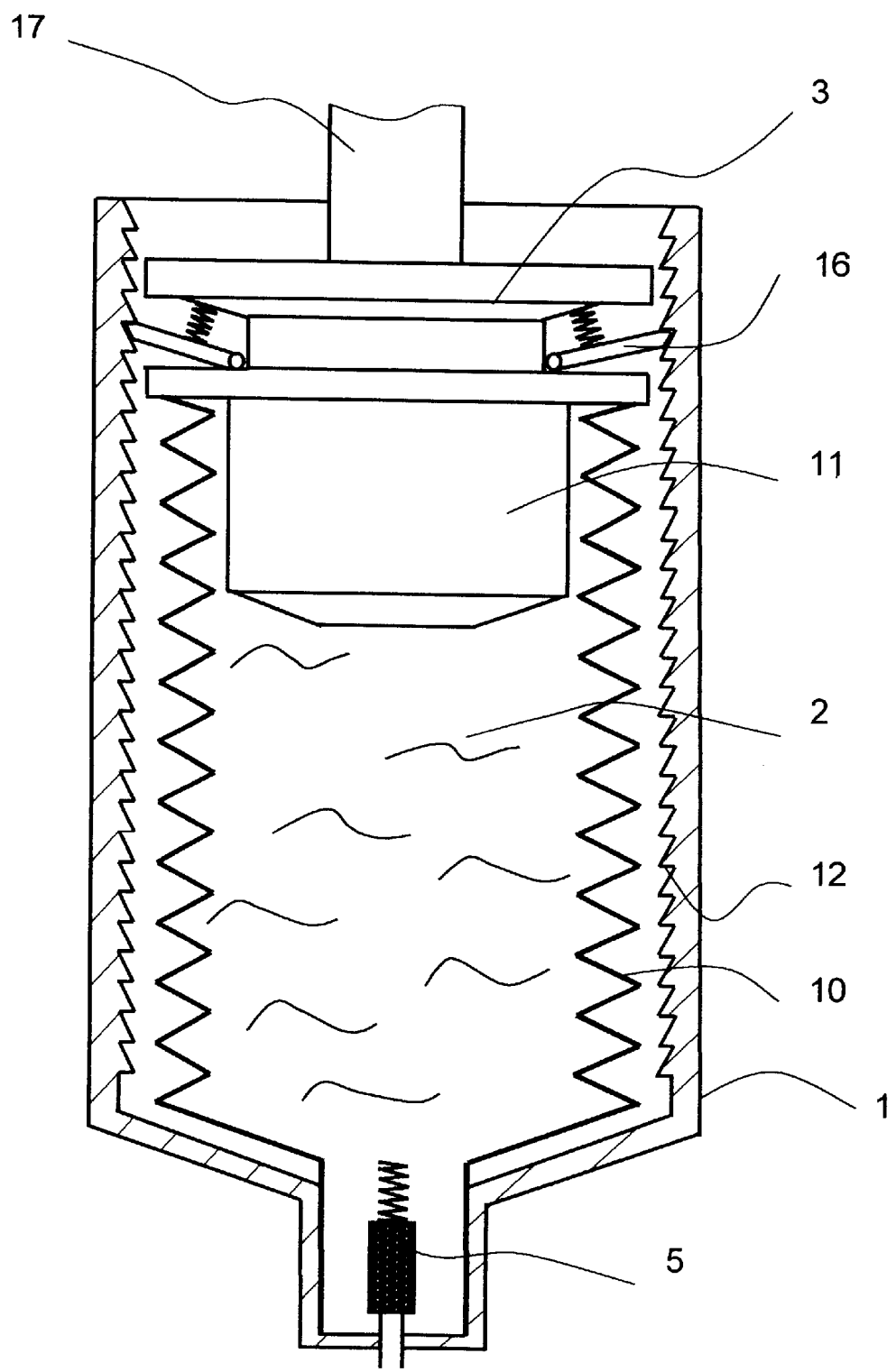
FIG. 2 is a sectional view of a second exemplary embodiment of an anesthetic container according to the present invention, in which identical components are designated by the same reference numbers.

FIG. 2 shows an alternative possibility of embodiment of an anesthetic container 1 with a bellows 10 made of a metallic material. This is for metering under pressure by means of a mechanical force applied by means of a piston actuating means 17. The liquid anesthetic is hermetically closed in the metallic bellows 10. The fine teeth of the protective tube 12 are used to lockingly receive a plurality of spring-loaded detent pawls 16 arranged on the piston. In addition, the piston has a displacer body 11 in the bellows 10, so that only a very small residual liquid anesthetic volume is left in the anesthetic container 1 with the bellows 10 pushed together completely. The other components correspond to those in FIG. 1.

An anesthetic container 1 according to the present invention with an anesthetic reserve space 2 for one L of liquid anesthetic corresponding to four times the amount held in the disposable bottles used commonly at present has an overall length of about 300 mm at an external diameter of about 130 mm. Under a working pressure of about 1.1 bar above the ambient pressure, the force on the piston is 1,000 N, max. Desflurane can thus be metered reliably at ambient temperatures of up to about 40° C. and an ambient pressure of 700 mbar.

While specific embodiments of the invention have been shown and described in detail to illustrate the application of the principles of the invention, it will be understood that the invention may be embodied otherwise without departing from such principles.

What is claimed is:

1. An anesthetic container comprising:
   a container structure defining an anesthetic reserve space with a metering opening and an open end;
   a liquid anesthetic disposed in said anesthetic reserve space;

a movable wall element closing said open end such that said metering opening is the only fluid passage from inside of said reserve space to outside of said reserve space, said wall element being in contact with said liquid anesthetic and moving with said liquid anesthetic to follow a surface of said liquid anesthetic upon a change in a volume of said liquid anesthetic as liquid anesthetic is metered out of said reserve space; and a metering element for metering the liquid anesthetic out of said reserve space to outside of said reserve space through said metering opening.

2. An anesthetic container in accordance with claim 1, further comprising: means for applying a force to said wall element to maintain said liquid anesthetic under pressure as said wall element is caused to follow the surface of the volume of said liquid anesthetic.

3. An anesthetic container in accordance with claim 1, further comprising:

a complementary metering element actuating said metering element inductively for metering the anesthetic.

4. An anesthetic container in accordance with claim 3, wherein said first metering element is a valve body and said another metering element is a valve coil.

5. An anesthetic container in accordance with claim 3, wherein said first metering element is an inductively actuated pump and said another metering element is a coil.

6. An anesthetic container in accordance with claim 1, further comprising: an anesthetic-specific coding including one of a transponder and a microchip element, whereby said anesthetic coding cooperates with an anesthesia apparatus with a code reader for metering the anesthetic and for reading the anesthetic-specific coding.

7. An anesthetic container in accordance with claim 1, further comprising: a toothed piston rod; and an elastomer ring wherein said movable wall element comprises a piston caused to follow the surface of the volume of said liquid anesthetic, said toothed piston rod being connected to said piston, said elastomer ring being provided on said container structure and cooperating with said piston rod as a detent pawl for teeth of said toothed piston rod.

8. An anesthetic container in accordance with claim 7, wherein the piston is provided with a displacer body in said anesthetic reserve space.

9. An anesthetic container in accordance with claim 1, wherein said movable wall element of said anesthetic reserve space comprises a piston and said container structure comprises a protective tube with successive teeth and with a bellows and said piston folds said bellows in said protective tube with said successive teeth corresponding to the anesthetic volume metered.

10. An anesthetic container in accordance with claim 9, wherein the piston is provided with a displacer body in said anesthetic reserve space.

11. An anesthetic container in accordance with claim 1, further comprising a filling level sensor for detecting a level of said surface of said liquid anesthetic.

12. An anesthetic container in accordance with claim 1, further comprising a temperature sensor for sensing a temperature of said liquid anesthetic.

13. An anesthetic container in accordance with claim 1, further comprising a displacement and/or force transducer detachably connected to said wall element wherein a current anesthetic volume and/or an anesthetic pressure is determined by said displacement and/or force transducer.

14. An anesthetic container system comprising:

a container part defining an anesthetic reserve space and having a metering opening and an open end;

a liquid anesthetic in said anesthetic reserve space;

a metering element connected to said container and disposed adjacent to or in said metering opening for regulating fluid flow through said metering opening from within said reserve space to outside of said reserve space;

a movable wall element part closing said reserve space open end such that said metering opening is the only fluid passage from within said reserve space to outside of said reserve space, said wall element applying pressure on said liquid anesthetic and being in contact with a surface of said liquid anesthetic whereby said anesthetic reserve space is free of gas and only filled by said liquid anesthetic, said wall element being disposed in said container part moving with said surface of said liquid anesthetic as liquid anesthetic flows out of said reserve space through said metering opening.

15. An anesthetic container system in accordance with claim 14, further comprising:

a wall moving mechanism for moving said wall element or allowing said wall element to move to follow said surface of said liquid anesthetic.

16. An anesthetic container system in accordance with claim 15, wherein said wall moving mechanism includes means for applying force to said wall element to maintain said liquid anesthetic under pressure as said wall element is caused to move to follow said surface of said liquid anesthetic.

17. An anesthetic container system in accordance with claim 16, further comprising:

an anesthesia apparatus with a breathing circuit and with a cooperating metering element inductively actuating said metering element for metering the liquid anesthetic to said breathing circuit.

18. An anesthetic container system in accordance with claim 17, wherein said anesthesia apparatus includes a plug in part with a plug in place having a portion with a shape complementary to a portion of said container part for receiving said container part to seat said container part, said cooperating metering element being supported by said plug in place adjacent to said metering element with said container part seated in said plug in place.

19. An anesthetic container system in accordance with claim 17, wherein said breathing circuit of said anesthesia apparatus includes a heater adjacent to said opening.

20. An anesthetic container system in accordance with claim 17, wherein said first metering element is an inductively actuated pump and said cooperating metering element is a coil.

21. An anesthetic container system in accordance with claim 18, further comprising: an anesthetic-specific coding including one of a transponder and a microchip element connected to said container and a reader for reading the anesthetic-specific coding connected to said plug in part.

22. An anesthetic container system in accordance with claim 15, further comprising: a toothed piston rod; and an elastomer ring wherein said movable wall element comprising a piston caused to follow the surface of the volume of said liquid anesthetic, said toothed piston rod being connected to said piston, said elastomer ring being provided on said container and cooperating with said piston rod as a detent pawl for teeth of said toothed piston rod.

23. An anesthetic container system in accordance with claim 15, wherein said movable wall element of said anesthetic reserve space comprises a piston and said container structure comprises a protective tube with successive teeth and with a bellows and said piston folds said bellows in said protective tube with said successive teeth corresponding to the anesthetic volume metered.

24. An anesthetic container system in accordance with claim 16, further comprising a filling level sensor for detecting a level of said surface of said liquid anesthetic the anesthetic volume.

25. An anesthetic container system in accordance with claim 16, further comprising a temperature sensor for sensing a temperature of said liquid anesthetic.

26. An anesthetic container system in accordance with claim 16, further comprising a displacement and/or force transducer detachably connected to said wall element wherein a current anesthetic volume and/or an anesthetic pressure is determined by said displacement and/or force transducer.

* * * * *